United States Patent [19]
Cagna et al.

[11] Patent Number: 5,885,078
[45] Date of Patent: *Mar. 23, 1999

[54] METHOD FOR CONSTRUCTING ACCURATELY FITTING FRAMEWORKS FOR ENDOSSEOUS IMPLANT-SUPPORTED DENTAL PROSTHESES

[75] Inventors: David R. Cagna, San Antonio; Robert E. Jones, Mission; Rajiv V. Nambiar, McAllen, all of Tex.

[73] Assignee: Board of Regents The University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 919,904

[22] Filed: Aug. 28, 1997

[51] Int. Cl.⁶ .................................................. A61C 13/12
[52] U.S. Cl. ............................................................ 433/172
[58] Field of Search .................................... 433/172, 173, 433/174, 175, 176

[56] References Cited

U.S. PATENT DOCUMENTS

| | | | |
|---|---|---|---|
| 4,062,119 | 12/1977 | Linkow et al. | 32/10 |
| 4,225,668 | 9/1980 | Bartoli | 433/176 |
| 4,492,840 | 1/1985 | Lex | 219/10.57 |
| 4,590,928 | 5/1986 | Hunt et al. | 623/13 |
| 4,931,016 | 6/1990 | Sillard | 433/172 |
| 5,049,075 | 9/1991 | Barrut | 433/167 |
| 5,174,954 | 12/1992 | Schaffer et al. | 420/463 |
| 5,246,368 | 9/1993 | Sillard | 433/167 |
| 5,630,717 | 5/1997 | Zuest et al. | 433/172 |

*Primary Examiner*—John J. Wilson
*Attorney, Agent, or Firm*—Arnold, White & Durkee

[57] ABSTRACT

The present invention discloses a device and method of achieving a passive fit between a dental implant-supported metal bar or framework and dental implants located within a patient's mouth. The present invention comprises the steps of fabricating the dental implant-supported metal bar, contacting the metal bar and the plurality of dental implant analogs within a dental cast, and correcting the fit of the metal bar by inductively heating the dental implant-supported bar, thereby achieve the desired passive fit.

16 Claims, 3 Drawing Sheets

METHOD FOR CONSTRUCTING ACCURATELY FITTING FRAMEWORKS FOR ENDOSSEOUS IMPLANT-SUPPORTED DENTAL PROSTHESES

FIELD OF THE INVENTION

The present invention relates to a method and apparatus for the accurate manufacturing and fitting of a metal bar or framework to endosseous dental implants located within a patient' mouth.

BACKGROUND OF THE INVENTION

Root-form, endosseous dental implants have been in common use in the United States for the treatment of edentulism and partial edentulism since the early 1980's. A root-form, endosseous, dental implant is a cylindrical device made of titanium or titanium alloy, typically 8–15 mm long and 4–6 mm wide. Its surface configuration may be threaded, acid etched, titanium plasma sprayed, or coated with hydroxyappatite. In general, when patients are missing some or all of their teeth, dental implants can be surgically placed into the jaw bone in the areas of the missing teeth. Following a 3–6 month healing period, a second surgical procedure is performed. During the second surgery, the dental implants are exposed and a cylindrical extension device, i.e., an abutment, is screw fastened to each dental implant. When the surgical wound is closed following this surgery, the abutments project through the gingival tissues so that approximately 1–3 mm of the abutment is apparent, extending into the oral cavity proper. At this point in the dental implant therapy, construction of a prosthesis is initiated. The final prosthesis is designed to directly or indirectly attach to the dental implants.

When a patient is missing several, but not all of his teeth, i.e., is partially edentulous, two or more dental implants may be surgically placed to support partial denture prostheses, i.e., "dental bridges". Typically in this scenario, the dental implants are surgically placed a minimum of approximately 3–5 mm apart in the area of the patient's jaw in which teeth are missing. Following healing, as previously described, the most common partial denture prosthesis involves the construction of a metal ceramic restoration. A metal substructure or framework is fabricated in an appropriate dental casting alloy. This metal framework may secondarily be veneered with a dental porcelain to create the illusion of natural dentition. This partial denture prosthesis is then fastened to the dental implants using a series of metal retaining screws, tightened to predetermined torque specifications. The implant supported partial denture prosthesis restores comfortable and efficient oral function, as well as providing acceptable aesthetic replacement of the patient's missing teeth.

Frequently, when a patient is missing all of his teeth, i.e., is edentalous, three to five implants will be surgically placed approximately 10–15 mm apart in the anterior aspect of the patient's edentulous jaw. Following healing, as previously described, a single metal framework or bar can be fabricated and fastened to each of the implants by small metal screws. A complete denture prosthesis is then constructed so that it may be clipped onto the metal bar at the patient's discretion. The metal bar screw fastened to the dental implants serves to stabilize, support and retain the complete denture. This mechanical advantage allows the patient to wear the complete denture prosthesis comfortably with assurance that the denture will not "fall out" at an inopportune and embarrassing moment. This physical and psychological security is frequently not available for patients that do not have the advantage of dental implant support for their complete denture. To this end, dental implants have served to improve a patient's quality of life.

Clinical research supports the ability of the human jaw bone to biologically accept implanted metallic structures, and maintain these structures in a healthy state. It is also the current belief of the dental profession that the application of excessive mechanical force to dental implants may adversely affect the surrounding bone. Excessive force may originate from a variety of sources. One such source is the constant mechanical force applied to implants when an inaccurately fitting metal bar or framework is screw fastened to the implants. This constant mechanical load on the system has been referred to as static prestress. If the fastened bar or framework does not fit accurately onto the dental implants, it may prestress or preload the system leading to (1) biological breakdown of bone contacting and surrounding the dental implants, and/or (2) premature mechanical failure of the retaining screws, dental implants or the metal bar or framework.

The present invention, as described herein, is equally applicable to the construction of metal bars and metal frameworks used in the dental prosthetic rehabilitation of patients missing some or all of their teeth. For simplicity of discussion, the metal bar, as described above in the restoration of edentulous patients, will be discussed in detail. However, it must be emphasized that the present invention may be applied equally well to both the metal bar and the metal framework supported by dental implants.

Bar fabrication involves the "lost wax" technique of metal casting. A wax or resin pattern of the proposed bar is created, incorporated in a gypsum-based investment material and cast in dental alloy, e.g., ADA type IV gold casting alloy consisting of 59% Au+23% Ag+13% Cu+4% Pd. Alternatively, the dental alloy may be nickel-chromium alloy or titanium alloy. Upon completion, the bar is properly finished and polished and placed in the patient's mouth. A single retaining screw is fastened to hold the bar in place, and the other bar-implant interfaces or junctions are visually inspected to assess the adequacy of bar adaptation. This approach of assessing fit may be referred to as the "single screw test". The accuracy of fit of the metal bar to the dental implants can be affected by a variety of factors during bar construction. However, a primary concern is the impact of solidification shrinkage of the cast metal alloy on the resultant three-dimensional accuracy of the bar. It is possible that distortion of the bar may be expressed in all three linear and three rotational dimensions.

As contemplated by the prior art, if adequate fit of the metal bar to the dental implants is not present, procedures directed at correction of the bar must be undertaken. Typically, the metal bar is sectioned, reoriented in the mouth or on the dental cast, and subjected to laboratory brazing procedures. The metal bar must again be placed on the dental implant using the "single screw test" to reassess the accuracy of fit. This sectioning-brazing procedure may have to be performed two, three, or four times before a visually assessed, accurate fit of the metal bar to the dental implants is achieved. A bar containing several soldered or brazed joints may be mechanically weakened such that normal masticatory loading will result in failure.

The present invention is directed to a method and apparatus for constructing accurately fitting, screw-retained, metal bars or metal frameworks for dental implant-assisted prostheses.

SUMMARY OF THE INVENTION

The present invention comprises, in a broad aspect, a method of achieving a passive fit between a dental implant bar and dental implant analogs of a dental cast of a patient's mouth, comprising the steps of aligning the dental implant bar with the dental implant analogs; contacting the dental implant bar and at least one of dental implant analogs; and adapting the dental implant bar to the dental implant analogs by inductively heating the dental implant bar to thereby soften the dental implant bar to achieve said passive fit. In an exemplary embodiment, the dental implant bar may be a dental casting alloy selected from the group consisting of gold alloy, titanium alloy, and nickel-chromium alloy. The contacting step may comprise joining the dental implant bar to at least one of the dental implant analogs by a retaining member. Alternately, the contacting step may comprise joining the dental implant bar to all of the dental implant analogs by a plurality of retaining members. In an exemplary embodiment, the adapting step may comprise placing an inductor coil around the dental implant bar and providing a desired alternating current to the inductor coil.

A method of the present invention may further comprise inspecting the dental implant bar and the dental implant analogs following the inductive heating to determine whether a passive fit has been attained. If such a fit has not been attained, the implant bar may be inductively reheated, so as to again soften the metal bar. After a desired fit has been attained, the dental implant bar may be connected to dental implants within the patient's mouth.

The present invention further includes a method of achieving a passive fit between a dental implant bar and a dental implants within a patient's mouth, comprising the steps of: aligning the dental implant bar with a dental cast of the mouth; adapting the dental implant bar onto dental implant analogs located within the dental cast; and inductively heating the dental implant bar sufficiently to stress relieve the dental implant bar until a desired passivity is achieved between the bar and the dental implant analogs, thereby achieving a passive fit. Then, the dental implant bar may be connected to dental implants within the patient's mouth.

DESCRIPTION OF ILLUSTRATIVE EMBODIMENTS

Figure 1A:
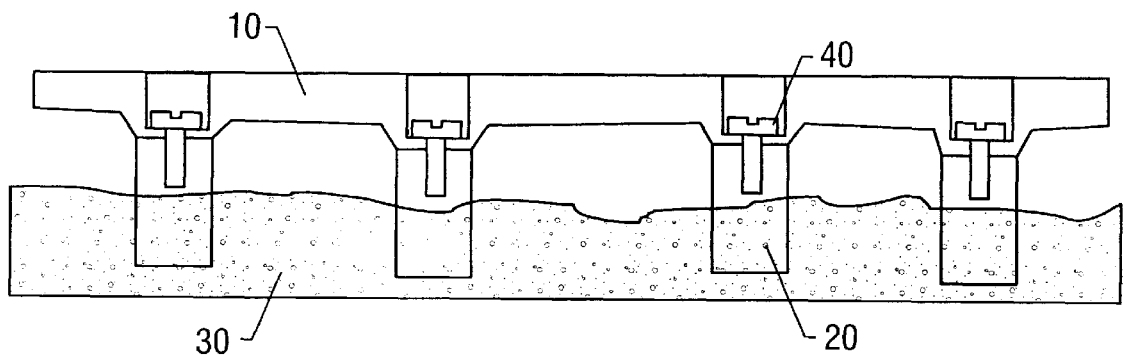
FIG. 1A is a front view of a metal bar supported by four dental implant analogs as placed within a dental model or cast according to the prior art.

As previously described, endosseous dental implant therapy as a treatment modality for edentulous and partially edentulous patients has been in common use in the United States since the early 1980's. When implants have been surgically placed, frequently a metal bar is fabricated and screw fastened to the implants. In exemplary embodiments, there may be four implants in place in the jaw; however, it is possible to surgically place more or fewer dental implants, given a wide range of clinical indications in various dental conditions. In exemplary embodiments, the metal bar may be constructed of a dental gold alloy, but other alloys such as nickel-chromium or titanium alloy may be used. The metal bar may be connected to the dental implants by various means, such as small retaining screws, set screws, cement or various adhesive materials.

The metal bar serves to retain, stabilize and support the overlying denture prosthesis. Passive and accurate fit of this bar to the implants may be critical to the longevity and success of the dental implants and the dental restoration, in total. A definition for "passive fit" of metal bar must account for the following considerations:

the lack of induced stress, or static prestress, within the metal bar upon intraoral placement and tightening of retaining screws to predetermined torque specifications;

the lack of static prestress within restorative components upon bar placement, including retaining screws, abutments and abutment screws; and the lack of static prestress within the implant fixture, at the bone-implant interface or in the periimplant bone tissue, upon bar placement.

As used herein, the term "passive", when applied to the metal bar or framework, means that once the metal bar is screw fastened to the dental implants, no undue or substantial force is induced in or around the dental implants, metal retaining screws, or metal bar. Ultimately, a metal bar clinically judged to exhibit acceptable fit, when in fact a truly "passive" fit is not physically present, may induce detrimental stress at the critical bone-implant interface or adversely load prosthetic components leading to premature biological and/or mechanical failure of the system. Clinical outcomes resulting from a lack of passive fit may include loosening or failure of the retaining screws, fracture of the metal bar, dental implant fracture, or destruction of the periimplant bone tissues.

Using present fabrication techniques, it is difficult to consistently and predictably produce metal bars that fit passively to the dental implants. Construction of the metal bar is the culmination of multiple clinical and laboratory procedures. Ultimate three-dimensional distortion of the metal bar leading to non-passive fit reflects the net contribution of accumulated dimensional inaccuracies originating from direct patient treatment procedures and laboratory fabrication methods and materials. A component of the overall, three-dimensional distortion of the metal bar or framework may originate from any or all of the following clinical and laboratory procedures: (1) abutment connection; (2) dental impression procedures; (3) dental cast fabrication; (4) clinical and laboratory verification procedures used to assess dental cast accuracy; (5) laboratory production of a wax or resin pattern for the metal bar or framework; (6) pattern investing, thermal elimination of contents from the mold and metal alloy casting; (7) procedures used to assess and correct the fit of the framework in the laboratory prior to clinical tryin, i.e., inherent inaccuracies in brazing and soldering procedures; (8) intraoral try-in and assessment procedures prior to final processing of the prosthesis; and (9) resin or dental porcelain processing and placement of the final prosthesis.

One aspect of the present invention resides in the application of induction heating technology to this dental patient treatment modality. Such a method aids in the production of metal bars that fit passively to the supporting dental implants. It is known that the fabrication of relatively accurate dental casts of the patient's mouth is possible through various dental impression techniques. Typically, these dental casts are fabricated in improved gypsum products, dental stone, or the like. The dental casts incorporate dental implant analogs or replicas that are accurately positioned within the dental cast relative to their three-dimensional orientation in the patient's mouth. A bar pattern is constructed in wax or resin, incorporated into a gypsum-based investing material, and cast in a variety of dental alloys. These procedures have been refined to the extent that "reasonably" accurate metal bar castings are possible if careful control is maintained on all factors impacting the process.

Although "reasonably" accurate, these metal bar castings may not be sufficiently accurate to be considered "passive", relative to previously mentioned criteria, when screw fastened onto the dental cast. In the prior art, applying full torque specifications to all metal screws used to retain the metal bar to the dental implants may unfortunately mechanically warp the metal bar into an "apparently" accurate fit. This "apparently" passive fit would, however, be inducing a static prestress in the system. As previously described, this static prestress may have detrimental biological and mechanical ramifications.

A method and apparatus according to the present invention may be used to locally apply an induction heating process to "stress relieve" the bar between adjacent dental implants, thereby resulting in a "truly" passive fit. Elimination of the otherwise statically prestressed condition will likely improve the longevity of the system, including facilitation of a biologic stability at the bone-implant interface, as well as improvement of the mechanical durability of the metal retaining screws and metal bar.

The present invention is an improvement over the prior art for several reasons. First, a method according to the present invention may be performed rapidly, i.e., on the order of minutes, and accurately produce a passive fit. Fabrication and correction techniques of the prior art are time intensive and inaccurate. Second, known techniques are destructive in their approach, i.e., cutting and braze rejoining, electrical discharge machining, and remake of unacceptable bars. The method according to the present invention is not destructive in its approach. Finally, the present invention permits truly accurate and passively fitting bars to be fabricated, whereas such bars are likely unattainable with current methodologies.

Although induction heating processes are in use in various industrial applications, no such process has been applied to the problems addressed by the present invention. Further, the present invention utilizes induction heating on a smaller scale than typical current industrial applications.

Since the production of a passively fitting metal bar is of primary importance to the overall success of dental implant therapy, and because current fabrication technologies cannot consistently and predictably produce accurate and passive metal bars or frameworks, the present invention for the predicable fabrication of passive metal bars or metal frameworks is a major breakthrough in the field of implant dentistry.

FIG. 1A is a front view of a metal bar 10 supported by four dental implants that may be used in accordance with the present invention. The bar may be cast in a variety of dental metal alloys, which in an exemplary embodiment may be a dental gold alloy, nickel-chromium alloy, or titanium alloy. As shown in FIG. 1A, a plurality of implant analogs 20 are accurately located within a dental cast 30 to which is fastened the metal bar 10 using metal retaining screws 40. The implant analogs 20 are replicas of actual dental implants, and are placed in the dental model 30 in the exact three-dimensional orientation as that found in the patient's mouth during an impression procedure. Conversely, if implant abutments are used in the dental therapy, the implant analogs 20 may be substituted by abutment analogs. The dental cast 30 is an exacting replica of the patient's jaw and houses the implant analogs 20 in proper three-dimensional orientation relative to the location of implants within the patient's mouth. The metal bar 10 may be connected to the implant analogs 20 by means of retaining screws 40 which, in an exemplary embodiment, may be made of a gold alloy, titanium alloy, or stainless steel.

Figure 1B:
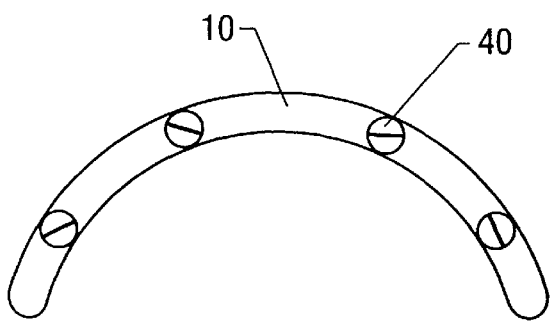
FIG. 1B is a top view of the metal bar of FIG. 1A.

FIG. 1B is a top view of the metal bar 10 having a plurality of retaining members 40 adapted thereon. As shown in FIG. 1B, the metal bar 10 is typically curved to follow the U-shape of a patient's jaw. In an exemplary embodiment, the dimension between two adjacent retaining screws 40, which correspond to locations of actual dental implants, may range from approximately 5 mm to approximately 15 mm. Again, as shown in FIG. 1B, four retaining screws 40 are shown. However, it is to be understood that more or fewer implants may be located in a particular patient's mouth.

Figure 1C:
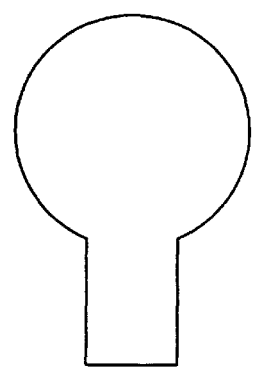
FIG. 1C illustrates a typical cross-sectional geometry of the metal bar shown in FIG. 1A.

FIG. 1C shows the typical cross-sectional geometry of the metal bar. As shown in FIG. 1C, the cross-section is generally circular with a generally rectangular portion extending therefrom. In an exemplary embodiment, the circular diameter may be approximately 1–2 mm, and the rectangular portion may be approximately 1 mm in length.

Figure 2A:
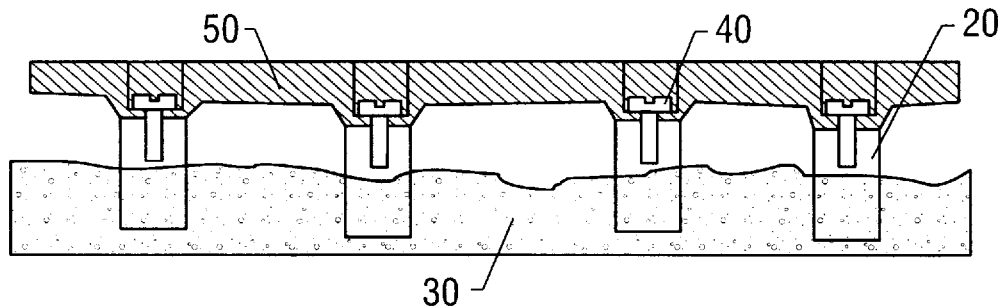
FIGS. 2A–2D illustrate a method of fitting a metal bar supported by four dental implants using the brazing or soldering process of the prior art.

FIGS. 2A–2D detail the prior art method of correcting the fit of a cast metal bar to a plurality of dental implants. An accurate dental cast 30 of the patient's mouth is made including accurate three-dimensional orientations of the dental implants, illustrated is in FIG. 2A as implant analogs 20. Then, as shown in FIG. 2A a wax or resin pattern 50 of the proposed bar is created on the dental cast 30 and is held in place by means of retaining screws 40. As shown in FIG. 2A, the wax or resin pattern 50 maintains a passive fit prior to investing and casting of the actual metal bar. The dental implant bar 10 is then cast from the wax or resin pattern 50 using known techniques.

Figure 2B:
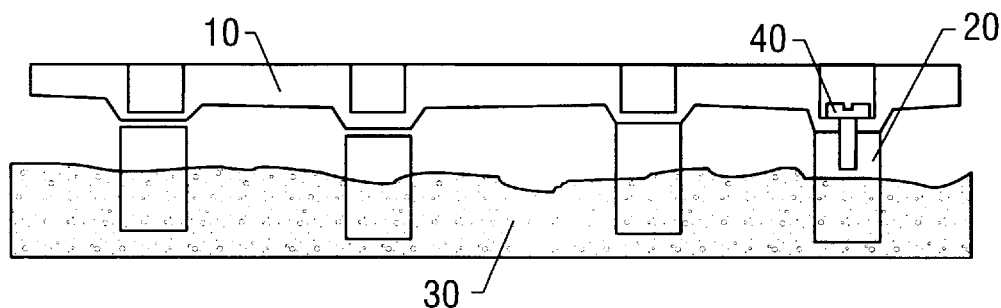

As shown in FIG. 2B, the completed metal bar 10 is first fastened to the implant analogs 20 located within the dental cast 30, by a single metal retaining screw 40. The metal bar 10 is then visually inspected to determine whether the fit between the bar 10 and the implant analogs 20 is accurate, i.e., passive. In most cases, the fit between the two is inaccurate following casting procedures. As shown in FIG. 2B the two left most implant analogs 20 have spaces between the analog 20 and the bar 10. This result is indicative of inaccurate or non-passive fit of the metal bar 10 to the implant analogs 20.

Figure 2C:
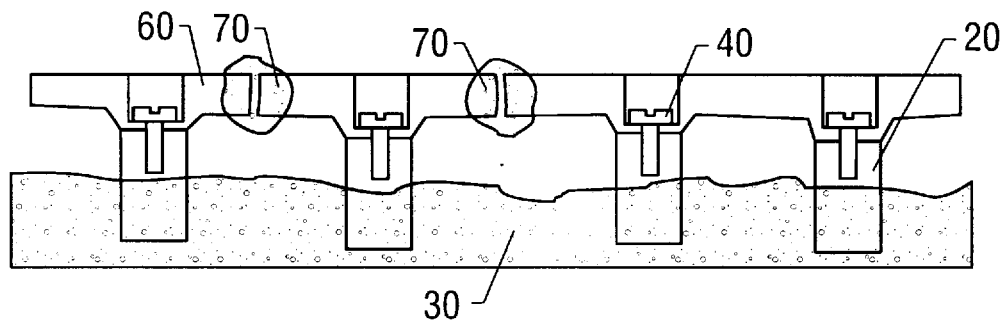
Figure 2D:
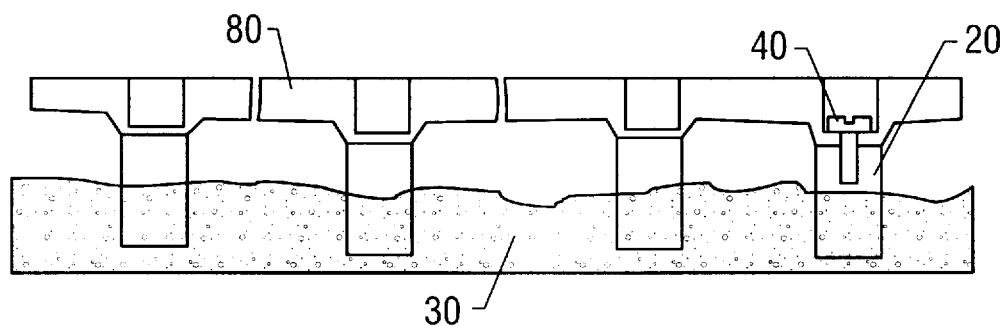

To remedy this situation, methods of the prior art have sectioned the bar 60 at one or more desired interimplant locations 70. In exemplary embodiments, the number of pieces may be between 1 and 3, depending on the accuracy of the fit. Segments of the sectioned metal bar 60 are then reoriented on the dental cast 30, with metal retaining screws 40 fastening the bar segments to the implant analogs 20. Separate segments of the sectioned metal bar 60 are then indexed in proper orientation with, for example, a resin material, as shown in FIG. 2C. The sectioned metal bar 60 is then rejoined using a brazing process. After brazing, the rejoined metal bar 80 is visually reinspected by placing the rejoined metal bar 80 onto the implant analogs 20 in the dental cast 30. The rejoined metal bar 80 is again connected by means of a single metal retaining screw 40, as shown in FIG. 2D, and a passive fit assessed. If the desired fit is not attained, the above steps may be repeated numerous times to achieve the desired passive fit.

Figure 3A:
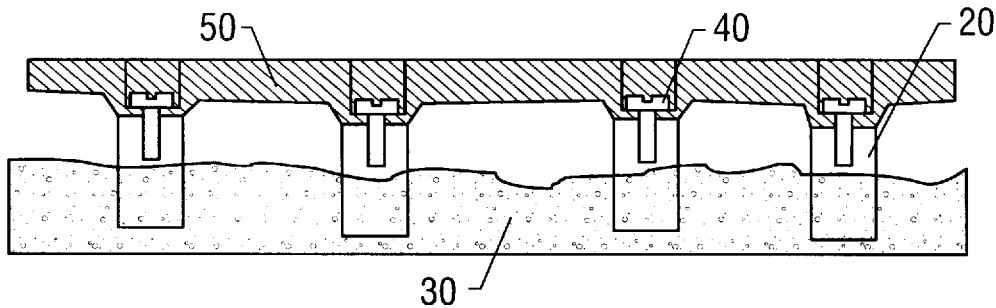
FIGS. 3A–3D illustrate an exemplary method of fitting a metal bar supported by four dental implants using the induction heating process in accordance with the present invention.
Figure 3B:
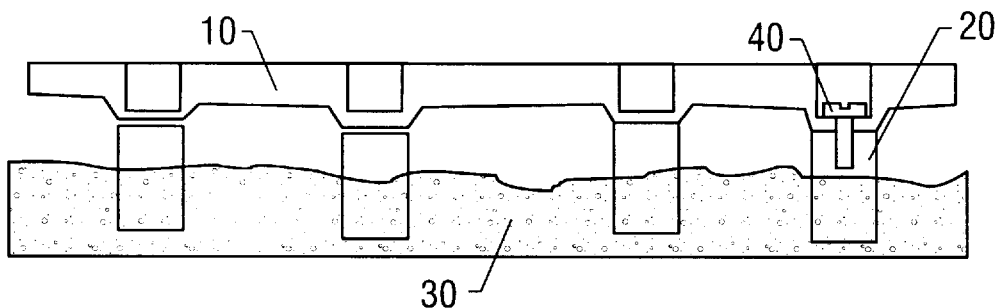

FIGS. 3A–3D detail a method according to the present invention. As shown in FIG. 3A, a wax or resin pattern 50 of the proposed bar is created and fastened to an accurate dental cast 30 with metal retaining screws 40. Prior to investing and casting, the wax or resin pattern 50 fits the dental cast 30 and incorporated implant analogs 20 passively. The bar 10 is then cast in a dental metal alloy according to known processes. The bar 10 is then placed on the dental cast 30 to determine whether the desired passive fit has been attained. A single metal retaining screw 40 may be used to fasten the metal bar 10 to the dental cast 30, as shown in FIG. 3B. The metal bar 10 is then visually inspected. Again, as in the prior art, the fit is typically inaccurate following the metal casting process. As shown in FIG. 3B the two left most implant analogs 20 demonstrate spaces between the analogs 20 and the metal bar 10. This result is indicative of inaccurate or non-passive fit of the metal bar 10 to the implant analogs 20.

Figure 3C:
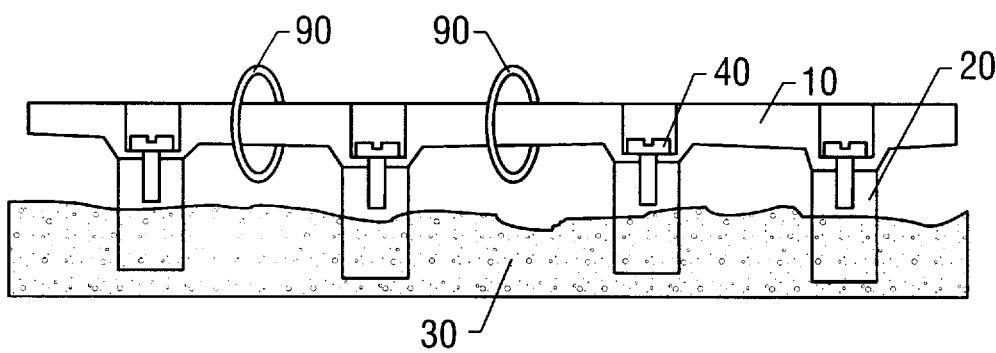

Next, as shown in FIG. 3C, the bar 10 is fastened to the implant analogs 20 in the dental cast 30 by placing a retaining screw 40 into each implant analog 20, thereby inducing stress, i.e., static prestress, within the metal bar 10 due to the inaccurate fit. An induction heating process according to the present invention may then be applied to relieve this static prestress. An induction heating apparatus employing standard technological principles may be used to provide the induced current. In an exemplary embodiment, the induction heating apparatus includes an alternating current generator, the output of which is connected to inductor coils 90.

As shown in FIG. 3C, inductor coils 90 may be used to supply the desired induced current to the metal bar 10. In an exemplary embodiment, there may be a plurality of sets of inductor coils 90 surrounding the metal bar 10. As shown in FIG. 3C, two sets of inductor coils 90 are present. However, more or fewer inductor coils 90 may be located around the metal bar 10. As shown in FIG. 3C, it is desired that inductor coils 90 be placed close to the metal bar 10 The selection of the desired current to be fed to the inductor coil 90 may be dependent upon the desired "power rate" and "induction field density." Parameter settings should be selected to supply enough power, fast enough, to provide highly localized heating of the bar section without allowing excessive conductive heating of the implant analogs 20 in the dental cast 30. It may be desired to wet the dental cast 30 or provide cooling to prevent heat damage if the requisite rate is not achievable.

Figure 3D:
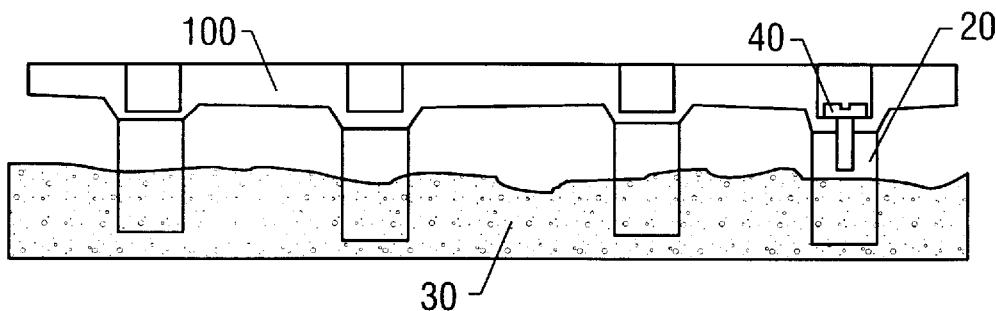

After the induction heating process, the corrected metal bar 100 is visually reinspected by placing the corrected metal bar 100 onto the implant analogs 20 in the dental cast 30. The corrected metal bar 100 is fastened to the dental cast 30 by means of a single metal retaining screw 40, as shown in FIG. 3D, and a passive fit assessed.

The induction heating process is an improvement over the prior art because the correction of inaccurate fit of the metal bar or framework occurs in a nondestructive, less time consuming manner. The process effects an intense, rapid heating induced directly into the objective material, i.e., the metal bar or framework. This induced heating is not limited by conventional heat diffusion through the objective material. Furthermore, the heating is highly localized and well controlled by shape and size of inductor coil. Thus, the present invention is a marked improvement over the prior art.

In an exemplary embodiment, the desired heating temperature may be approximately 75% of the melting temperature, locally, of the dental casting alloy used to fabricate the metal bar. The induction heating apparatus may apply the desired current for between approximately 2 seconds and approximately 30 seconds. The heating time is reasonably independent of the amount of fit correction required.

The induction heating process thereby relieves the static prestress that may otherwise be imparted by the metal bar 10 as the metal bar 10 is screw fastened to the implant analogs 20 within the dental cast 30. After the induction heating process, the metal retaining screws 40 are removed from all except one of the implant analogs 20, as shown in FIG. 3D. The corrected metal bar 100 is then reinspected to determine whether a passive fit has been obtained. Generally, only one heating process is required to obtain the desired fit, however, it may be possible to perform the induction heating process of the present invention multiple times to achieve the desired result. After a passive fit has been verified, the corrected metal bar 100 may be removed from the dental cast 30 and placed in the patient's mouth.

Further modification and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having benefit of this description of the invention.

What is claimed is:

1. A method of achieving a passive fit between a dental implant bar and a plurality of dental implant analogs of a dental cast of a patient's mouth, comprising the steps of:
    aligning said dental implant bar with said plurality of dental implant analogs;
    contacting said dental implant bar and at least one of said plurality of dental implant analogs; and
    adapting said dental implant bar to said plurality of dental implant analogs by inductively heating said dental implant bar to thereby soften said dental implant bar to achieve said passive fit.

2. The method of claim 1, wherein said dental implant bar comprises a dental casting alloy.

3. The method of claim 2, wherein said dental casting alloy is selected from the group consisting of gold alloy, nickel-chromium alloy and titanium alloy.

4. The method of claim 1, further comprising fabricating said dental implant bar by casting said dental implant bar from a wax or resin pattern.

5. The method of claim 1, wherein said contacting step comprises joining said dental implant bar to said at least one of said plurality of dental implant analogs by at least one retaining member.

6. The method of claim 1, wherein said contacting step comprises joining said dental implant bar to said plurality of dental implant analogs by a plurality of retaining members.

7. The method of claim 1, wherein said adapting step comprises placing an inductor coil around said dental implant bar and providing a desired alternating current to said inductor coil.

8. The method of claim 1, further comprising inspecting said dental implant bar and said plurality of dental implant analogs following the inductive heating to determine whether said passive fit has been attained.

9. The method of claim 8, further comprising inductively reheating said dental implant bar if said passive fit has not been attained, so as to again soften the metal bar.

10. The method of claim 1, further comprising attaching said dental implant bar to a plurality of dental implants within said patient's mouth.

11. A method of achieving a passive fit between a dental implant bar and a plurality of dental implants within a patient's mouth, comprising the steps of:

aligning said dental implant bar with a dental cast of said patient's mouth;

adapting said dental implant bar onto a plurality of dental implant analogs located within said dental cast; and inductively heating said dental implant bar sufficiently to stress relieve said dental implant bar and until a desired passivity is achieved between said dental implant bar and said plurality of dental implant analogs, thereby achieving said passive fit between said dental implant bar and said plurality of dental implants.

12. The method of claim 11, further comprising contacting said dental implant bar to said plurality of dental implants.

13. The method of claim 12, wherein said adapting step comprises joining said dental implant bar to said plurality of dental implants by a plurality of retaining members.

14. The method of claim 13, wherein said retaining members comprise retaining screws.

15. The method of claim 11, wherein said adapting step comprises joining said dental implant bar to at least one of said plurality of dental implant analogs by a retaining member.

16. The method of claim 11, wherein said inductive heating step comprises placing at least one inductor coil around said dental implant bar and providing a desired alternating current to said inductor coil.

* * * * *